US00PP29553P3

(12) United States Plant Patent
Wood

(10) Patent No.: US PP29,553 P3
(45) Date of Patent: Jul. 31, 2018

(54) ***VIBURNUM* PLANT NAMED 'SMNVPTFD'**

(50) Latin Name: *Viburnum plicatum tomentosum*
Varietal Denomination: SMNVPTFD

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 40 days.

(21) Appl. No.: 15/530,098

(22) Filed: Dec. 2, 2016

(65) Prior Publication Data

US 2018/0160595 P1 Jun. 7, 2018

(51) Int. Cl.
*A01H 5/02* (2018.01)
*A01H 5/12* (2018.01)

(52) U.S. Cl.
USPC ..... Plt./226
CPC ..... *A01H 5/02* (2013.01); *A01H 5/12* (2013.01)

(58) Field of Classification Search
USPC ..... Plt./226
See application file for complete search history.

*Primary Examiner* — Anne Marie Grunberg
(74) *Attorney, Agent, or Firm* — Cassandra Bright

(57) ABSTRACT

A new and distinct cultivar of *Viburnum* plant named 'SMNVPTFD' is disclosed, characterized by a distinctive low growing, prostrate plant habit. Plants produce large, showy white flowers. The new variety is a *Viburnum* normally produced as an outdoor garden or container plant.

5 Drawing Sheets

Latin name of the genus and species: *Viburnum plicatum tomentosum.*
Variety denomination: 'SMNVPTFD'.

BACKGROUND OF THE INVENTION

The present invention comprises a new and distinct variety of *Viburnum*, hereinafter referred to by the cultivar name 'SMNVPTFD'. This new *Viburnum* was developed through a breeding program in Grand Haven, Mich. The objective of the breeding program was to develop new *Viburnum* varieties with dwarf plant forms and interesting flower habits and colors. 'SMNVPTFD' was selected from a population of seedlings grown from an open-pollinated seed parent *Viburnum plicatum tomentosum* 'Fujianensis', unpatented with a group of unnamed, unpatented *Viburnum plicatum tomentosum* pollinators. The open-pollination resulting in the new variety was conducted during 2004. Selection of the new variety was made during 2008.

The first asexual propagation of 'SMNVPTFD' was carried out during 2008 by softwood cuttings at a commercial nursery in Grand Haven, Mich. 'SMNVPTFD' has been found to retain its distinctive characteristics through successive asexual propagations. Approximately 5 to 6 generations have been propagated, with the new variety characteristics reproduced true to type.

SUMMARY OF THE INVENTION

The following are the most outstanding and distinguishing characteristics of this new cultivar when grown under standard horticultural practices at Grand Haven, Mich.:

1. Low growing plants with a prostrate habit.
2. Large, showy flowers.
3. Floriferous plants

COMPARISON WITH THE KNOWN PARENT

'SMNVPTFD' is distinguished from its female parent *Viburnum* 'Fujianensis' in the following:

1. The new variety produces orange fruit, the female parent produces yellow fruit.
2. The new variety grows to a mature height of 6 to 9 feet, the female parent grows to 5 to 6 feet at maturity.
3. The new variety has larger leaves then the seed parent.

COMMERCIAL COMPARISON

'SMNVPTFD' is similar to the commercial variety *Viburnum* 'Shoshoni', unpatented, in most horticultural characteristics. 'SMNVPTFD' however differs in the following:

1. Plants of the new variety are shorter at maturity than plants of 'Shoshoni'. Plants of the new variety reach a mature height around 6 to 9 feet, this comparator reaches a mature height around 5 to 6 feet.

DESCRIPTION OF THE PHOTOGRAPHS

This new *Viburnum* is illustrated by the accompanying photographs which show the plant's form, foliage and inflorescences. The colors shown are as true as can be reasonably obtained by conventional photographic procedures. Plants were grown in Grand Haven, Mich.

Figure 1:
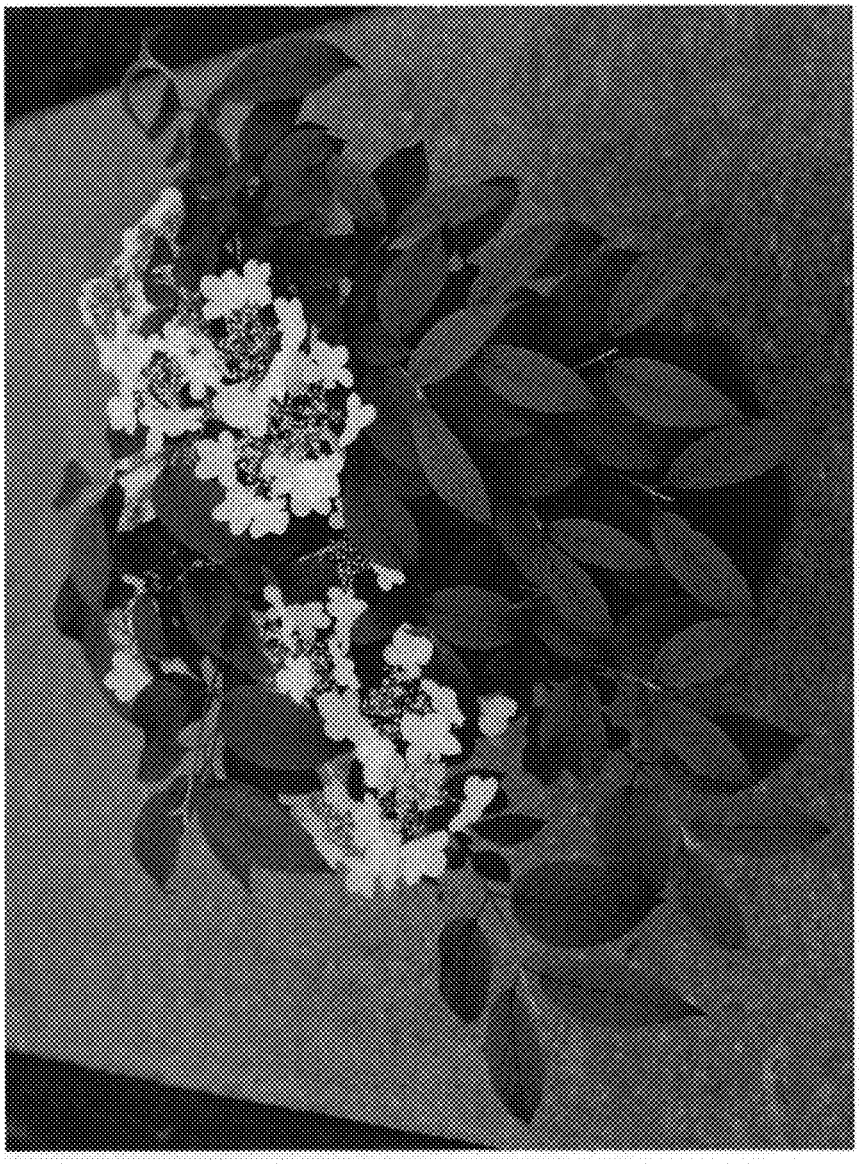

FIG. 1. Shows a flowering plant of 'SMNVPTFD' in a 2 gallon container at approximately 2 years old during Summer. Plants were grown in a polyhouse.

Figure 2:
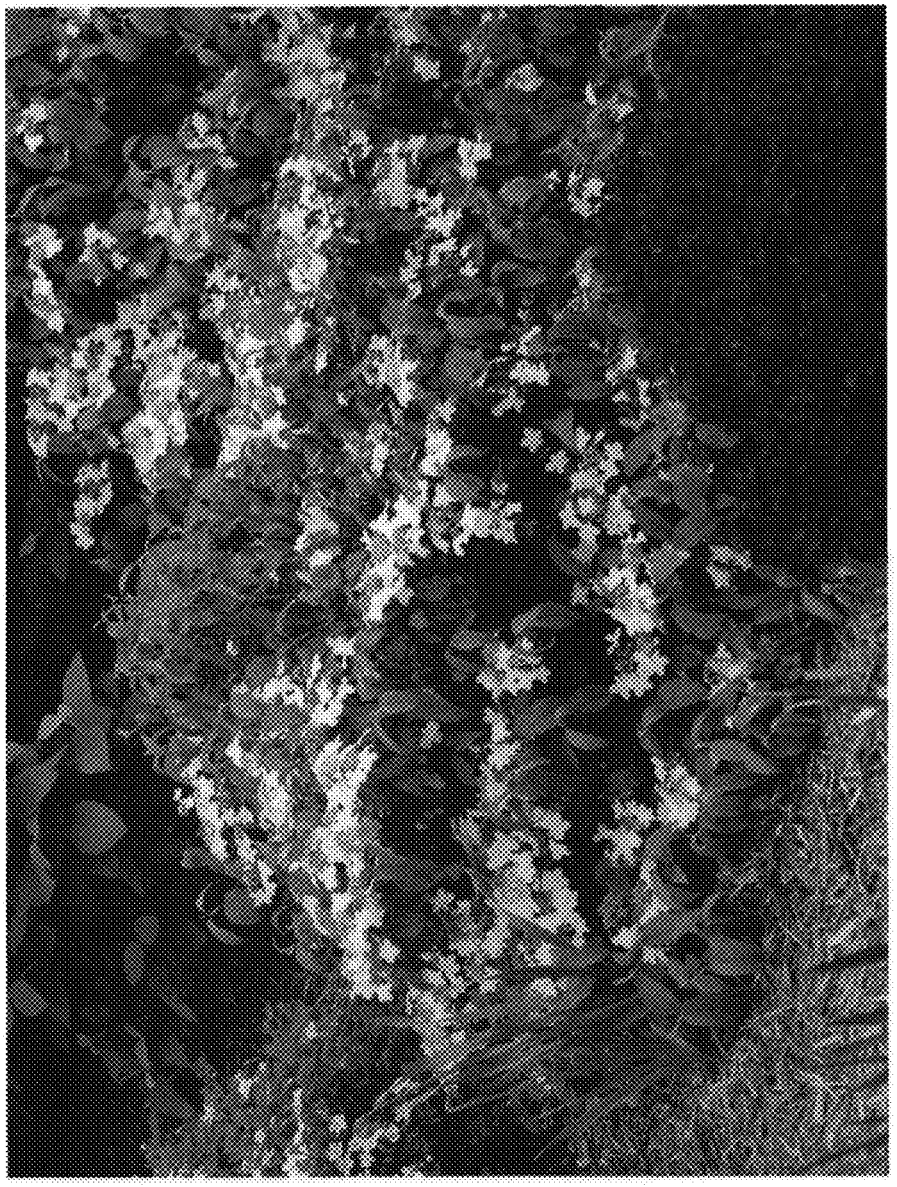

FIG. 2 Shows a mature plant of approximately 3 years, grown outdoors in Grand Haven, Mich.

Figure 3:
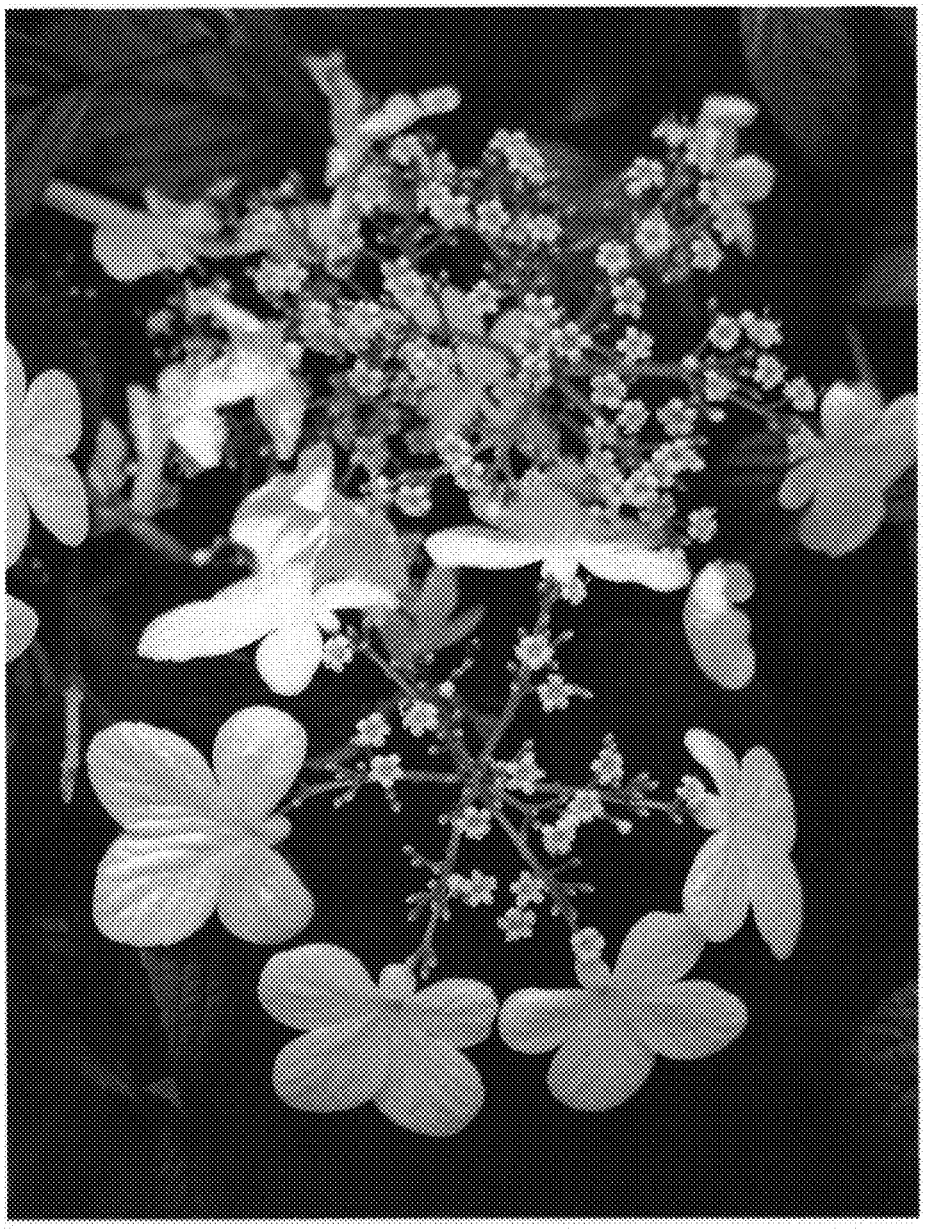

FIG. 3. Shows a close-up view of flowers.

Figure 4:
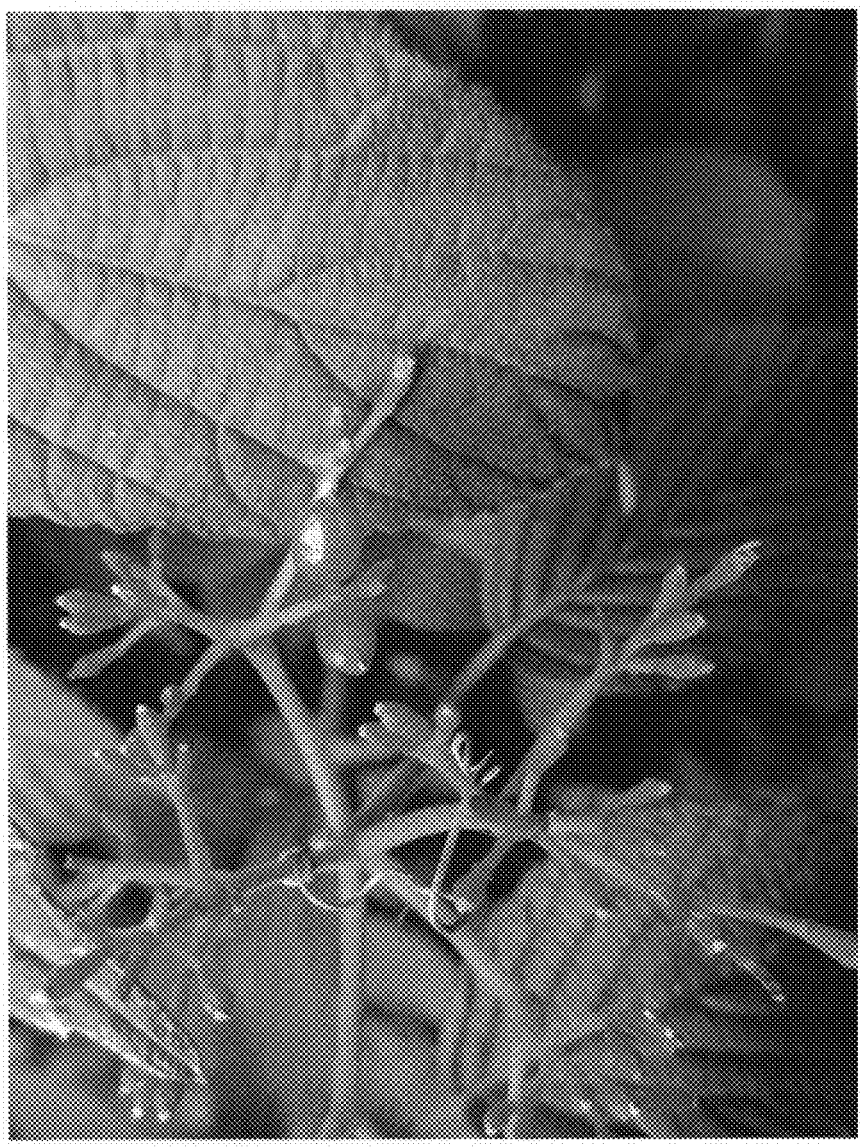

FIG. 4. Shows a close-up view of fruits.

Figure 5:
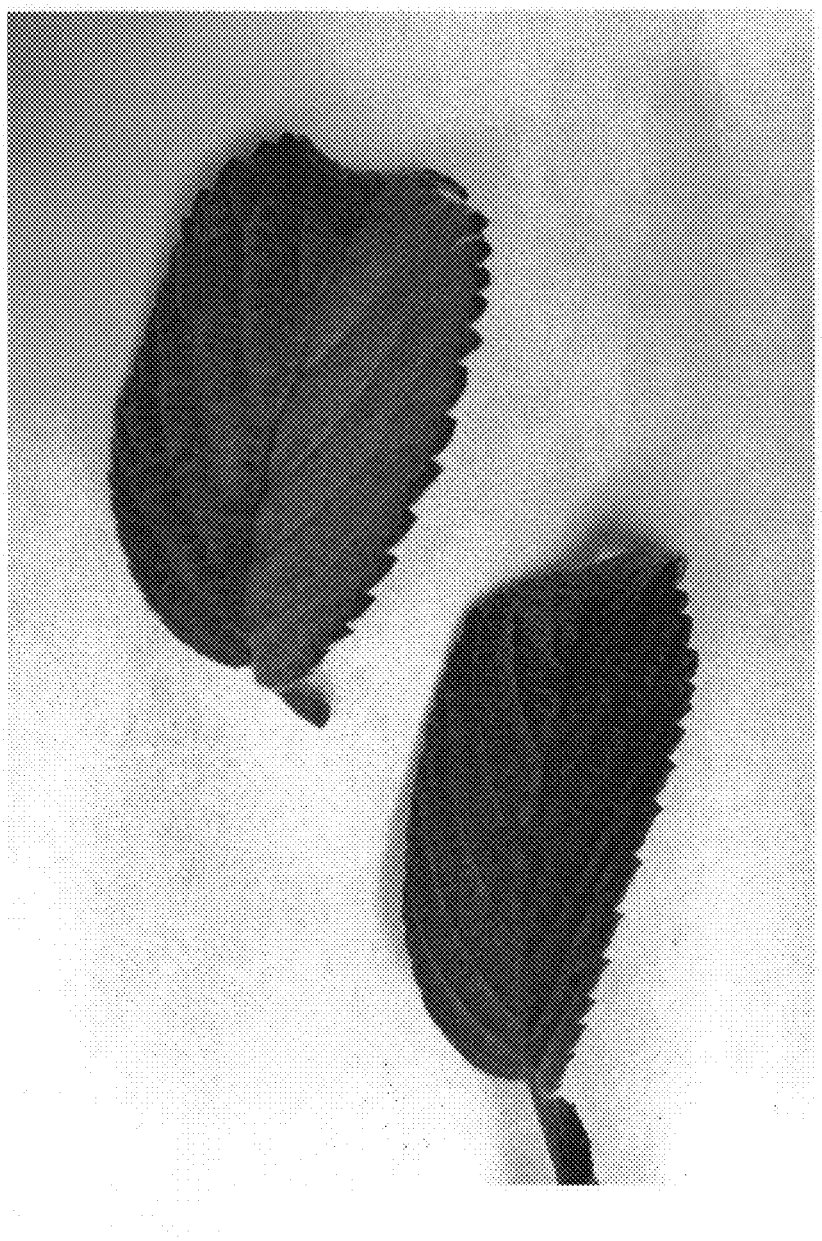

FIG. 5 Shows Fall foliage color.

DESCRIPTION OF THE NEW CULTIVAR

In the following description, color references are made to The Royal Horticultural Society Colour Chart 2015 except where general terms of ordinary dictionary significance are used. The following observations and measurements describe 'SMNBDO' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

DETAILED BOTANICAL DESCRIPTION

Botanical classification: *Viburnum plicatum tomentosum* 'SMNVPTFD'.

Propagation:

*Typical method*.—Softwood cuttings.

*Time to initiate rooting*.—28 days at approximately 18° C.

*Time to produce a rooted young plant*.—About 35 days at approximately 18° C.

*Root description*.—Dense, free branching roots of moderate thickness. Colored yellow-white, not accurately measured with an R.H.S. chart.

Plant description:

*Age of plant described*.—About 2 years in a 2 gallon container.

*Growth habit*.—Perennial shrub. Low growing, prostrate, slightly mounded.

*Height*.—21 cm.

*Width*.—54 cm.

*Growth rate*.—Moderate.

Branches:

*Branching habit*.—Basal branching, or near base.

*Lateral branch quantity*.—Average 14.

*Lateral branch length*.—Average 22 cm.

*Lateral branch diameter*.—Average 3 mm.

*Branch angle*.—20 to 30 degrees from plane of pot, forming outward spreading.

*Branch strength*.—Strong.

*Branch texture*.—Pubescent.

*Branch color*.—Current year growth: near Grey-Brown 199A, overlaying a background of Green 138B. Tip(above first internode) near Greyed-Green 192D.

*Internode length*.—4.5 to 7.5 cm.

Foliage:

Leaves:

*Persistence*.—Semi-evergreen.

*Arrangement*.—Opposite, simple.

*Length*.—Avg. range 5 to 12 cm. Larger leaves near top on newest growth.

*Width*.—Avg. range 3.5 to 5.5 cm.

*Shape*.—Narrow ovate, to nearly elliptic.

*Apex*.—Acuminate.

*Base*.—Obtuse.

*Margin*.—Serrate.

*Texture upper surface*.—Smooth, ridged.

*Texture lower surface*.—Pubescent.

*Color*.—Immature: Upper: Near Green 137B. Lower: Near Green 137B, covered in fuzzy pubescence colored Yellow-Green 145A. Mature: Upper: Near Green 137A. Lower: Near Green 137A. Fall foliage color: Upper: Mainly near Yellow-Green N144A, covered or half covered with Greyed-Purple 185A. Many leaves only turn half Greyed-Red. Lower: Near Yellow-Green N144A, lightly covered 185A.

Venation:

*Type*.—Pinnate.

*Color*.—Upper: Majority same a leaf blade, approximately ⅓ of midrib from the petiole is colored Greyed-Red 182B. Lower: Majority same a leaf blade, approximately ⅓ of midrib from the petiole is colored Greyed-Red 182C.

Petiole:

*Length*.—Average range 1.5 to 2.0 cm.

*Width*.—Average 2.0 mm.

*Texture*.—Soft, fuzzy pubescence.

*Color*.—New growth upper surface: Near Greyed-Red 178A. New growth lower surface: Near Greyed-Red 178B.

Durability: Good durability to environmental stressors.

Inflorescence:

*Description*.—Single salverform flowers arranged in a terminal cyme. Sterile flowers consistently arranged on the outermost edge of the cyme.

*Flowering season*.—Late Spring to Summer.

*Flower longevity*.—2-3 weeks.

*Fragrance*.—Faint, bitter.

*Inflorescence per plant*.—Average 16.

*Number of flowers per inflorescence*.—46 to 70 per cyme.

*Inflorescence height*.—Avg. 5.8 cm.

*Inflorescence diameter*.—Avg. 7.8 cm.

Flowers:

*Flower diameter*.—Avg. 2.5 cm sterile flowers, Avg. 4 mm fertile flowers.

*Flower depth*.—Avg. 2.0 cm sterile flowers Avg. 3 mm fertile flowers.

*Flower aspect*.—Upright and outward.

*Persistent of self-cleaning*.—Self-Cleaning.

*Flower bud*.—Length: 2 mm. Diameter: 2 mm. Shape: Round. Color: Immature: Yellow 4C, mature Yellow-White 158B.

*Petals fertile and sterile flowers*.—Number: Sterile: 4 to 5. Fertile: 5. Arrangement: Whorl. Length: Sterile: Avg. 4 to 17 mm sterile flowers, Fertile: Avg. 2 mm. Width: Sterile: Avg. 4 to 11 mm. Fertile: 2 mm. Shape: Sterile: Obovate. Fertile: Elliptic. Apex: Sterile: Obtuse. Fertile: Acute. Base: Fused. Margin: Entire. Texture: Glabrous, silky upper and lower surfaces. Color: Sterile: Immature upper surface: White 155D. Immature lower surface: White 155D. Mature upper surface: White 155D. Mature lower surface: White 155D. Fertile: Immature upper surface: Yellow-White 158A. Immature lower surface: Yellow-White 158A. Mature upper surface: Yellow-White 158A. Mature lower surface: Yellow-White 158A.

Sepals:

*Number*.—5.

*Arrangement*.—Whorl.

*Length*.—Sterile: 3 mm. Fertile: less than 0.1 cm.

*Width*.—Sterile: 1 mm. Fertile: less than 0.1 cm.

*Shape*.—Lanceolate.

*Apex*.—Acute.

*Base*.—Fused.

*Margin*.—Entire.

*Texture*.—Glabrous upper and lower surfaces.

*Color*.—Yellow-Green 145B, upper and lower surfaces.

Peduncle:

*Length*.—Avg. 7.4 cm.

*Width*.—Avg. 2 mm.

*Color*.—Upper section Yellow-Green 152D, lower section 144A.

*Texture*.—Fuzzy, small trichomes.

*Angle*.—Upright and outward.

*Strength*.—Moderate.

Pedicels:

*Length*.—Avg. 8 mm.

*Diameter*.—Avg. 1 mm.

*Texture*.—Fuzzy, small trichomes.

*Color*.—Yellow-Green 146C.

*Strength*.—Strong.

Reproductive organs:

*Gynoecium*.—Pistil number: 1. Pistil length: Less than 1 mm. Stigma shape: Rounded. Stigma color: Yellow-Green 144C. Style length: Less than 1 mm. Style color: Yellow-Green 144C.

*Androecium*.—Stamen number: 5. Filament length: 1 mm. Filament color: Yellow-White 158A. Anther shape: Oblong. Anther Length: 0.5 mm. Anther color: Yellow-White 158B. Amount of pollen: Scant. Pollen color: Yellow 6B.

OTHER CHARACTERISTICS

Fruit: Approximately 10 to 20 fruits per inflorescence. Ovate drupe 6 mm long, 4 mm in diameter, colored Red 53A, smooth texture.

Seed: 1 seed per fruit. 5 mm long, 4 mm wide. Ovate, colored near Greyed-Yellow 162C.

Disease and insect resistance: No significant disease or pest resistance nor susceptibility have been observed.

Cold hardiness: Observed to tolerate temperatures between −31° C. and 38° C.

What is claimed is:

1. A new and distinct *Viburnum* plant named 'SMN-VPTFD' as illustrated and described herein.

* * * * *